(12) United States Patent
Aizenberg et al.

(10) Patent No.: US 7,666,665 B2
(45) Date of Patent: Feb. 23, 2010

(54) LOW ADSORPTION SURFACE

(75) Inventors: Joanna Aizenberg, New Providence, NJ (US); Paul Kolodner, Hoboken, NJ (US); Joseph Ashley Taylor, Springfield, NJ (US)

(73) Assignee: Alcatel-Lucent USA Inc., Murray Hill, NJ (US)

( * ) Notice: Subject to any disclaimer, the term of this patent is extended or adjusted under 35 U.S.C. 154(b) by 161 days.

(21) Appl. No.: 11/216,373

(22) Filed: Aug. 31, 2005

(65) Prior Publication Data

US 2007/0048858 A1 Mar. 1, 2007

(51) Int. Cl.
*C12M 3/00* (2006.01)
(52) U.S. Cl. .................................... 435/287.3
(58) Field of Classification Search .............. 435/287.2, 435/7.2; 436/514
See application file for complete search history.

(56) References Cited

U.S. PATENT DOCUMENTS

| | | | |
|---|---|---|---|
| 3,454,686 A | 7/1969 | Jones | |
| 3,670,130 A | 6/1972 | Greenwood | |
| 4,030,813 A | 6/1977 | Kohashi et al. | |
| 4,118,270 A | 10/1978 | Pan et al. | |
| 4,137,060 A | 1/1979 | Timmermann | |
| 4,338,352 A | 7/1982 | Bear et al. | |
| 4,406,732 A | 9/1983 | Kayoun | |
| 4,569,575 A | 2/1986 | Le Pesant et al. | |
| 4,653,847 A | 3/1987 | Berg et al. | |
| 4,671,609 A | 6/1987 | Khoe et al. | |
| 4,708,426 A | 11/1987 | Khoe | |
| 4,783,155 A | 11/1988 | Imataki et al. | |
| 4,784,479 A | 11/1988 | Ikemori | |
| 4,867,521 A | 9/1989 | Mallinson | |
| 4,948,214 A | 8/1990 | Hamblen | |
| 5,248,734 A | 9/1993 | Ober et al. | |
| 5,348,687 A | 9/1994 | Beck et al. | |
| 5,412,746 A | 5/1995 | Rossberg et al. | |
| 5,428,711 A | 6/1995 | Akiyama et al. | |
| 5,486,337 A | 1/1996 | Ohkawa | |
| 5,518,863 A | 5/1996 | Pawluczyk | |
| 5,659,330 A | 8/1997 | Sheridon | |
| 5,665,527 A | 9/1997 | Allen et al. | |
| 5,922,299 A | 7/1999 | Bruinsma et al. | |
| 5,948,470 A | 9/1999 | Harrison et al. | |
| 6,014,259 A | 1/2000 | Wohlstadter | |
| 6,027,666 A | 2/2000 | Ozin et al. | |
| 6,103,199 A * | 8/2000 | Bjornson et al. ............ | 422/100 |
| 6,185,961 B1 | 2/2001 | Tonucci et al. | |
| 6,319,427 B1 | 11/2001 | Ozin et al. | |
| 6,329,070 B1 | 12/2001 | Sass et al. | |
| 6,369,954 B1 | 4/2002 | Berge et al. | |
| 6,379,874 B1 | 4/2002 | Ober et al. | |
| 6,387,453 B1 | 5/2002 | Brinker et al. | |
| 6,409,907 B1 | 6/2002 | Braun et al. | |
| 6,465,387 B1 | 10/2002 | Pinnavaia et al. | |
| 6,471,761 B2 | 10/2002 | Fan et al. | |
| 6,473,543 B2 | 10/2002 | Bartels | |
| 6,538,823 B2 | 3/2003 | Kroupenkine et al. | |
| 6,545,815 B2 | 4/2003 | Kroupenkine et al. | |
| 6,545,816 B1 | 4/2003 | Kroupenkine et al. | |
| 6,891,682 B2 | 5/2005 | Aizenberg et al. | |
| 7,195,872 B2 * | 3/2007 | Agrawal et al. ................ | 435/6 |
| 7,195,875 B2 * | 3/2007 | Keys et al. ..................... | 435/6 |
| 7,204,298 B2 | 4/2007 | Hodes et al. | |
| 2002/0125192 A1 | 9/2002 | Lopez et al. | |
| 2003/0020915 A1 | 1/2003 | Schueller et al. | |
| 2003/0148401 A1 | 8/2003 | Agrawal et al. | |
| 2004/0058450 A1 | 3/2004 | Pamula et al. | |
| 2004/0191127 A1 | 9/2004 | Kornblit et al. | |
| 2005/0039661 A1 | 2/2005 | Kornblit et al. | |
| 2005/0069458 A1 | 3/2005 | Hodes et al. | |
| 2006/0172189 A1 | 8/2006 | Kolodner et al. | |
| 2007/0048858 A1 | 3/2007 | Aizenberg et al. | |
| 2007/0056853 A1 | 3/2007 | Aizenberg et al. | |
| 2007/0059213 A1 | 3/2007 | Aizenberg et al. | |
| 2007/0059489 A1 | 3/2007 | Hodes et al. | |
| 2007/0237025 A1 | 10/2007 | Krupenkin et al. | |
| 2007/0272528 A1 | 11/2007 | Gasparyan et al. | |

FOREIGN PATENT DOCUMENTS

| | | |
|---|---|---|
| DE | 19623270 A1 | 1/1998 |
| DE | 19705910 C1 | 6/1998 |
| DE | 19704207 A1 | 8/1998 |
| EP | 0 290 125 | 11/1988 |

(Continued)

OTHER PUBLICATIONS

U.S. Appl. No. 10/040,017, filed Jan. 4, 2002, Megens et al.

(Continued)

*Primary Examiner*—Ann Y Lam
(74) *Attorney, Agent, or Firm*—Hitt Gaines, PC

(57) ABSTRACT

A device comprising an analytical sample substrate having at least one region that comprises a plurality of sample-support-structures. Each of the sample-support-structures have at least one dimension of about 1 millimeter or less. A sum of areas of contact surfaces of the sample-support-structures is substantially less than a total area of the region. The contact surfaces define a prescribed sample path to an analytical depot located on the analytical sample substrate.

17 Claims, 10 Drawing Sheets

FOREIGN PATENT DOCUMENTS

| | | | |
|---|---|---|---|
| EP | 1120164 | | 8/2001 |
| WO | WO 99/18456 | | 4/1999 |
| WO | WO 99/54730 | | 10/1999 |
| WO | WO 01/31404 | A1 | 5/2001 |
| WO | WO 01/42540 | | 6/2001 |
| WO | WO 01/51990 | | 7/2001 |
| WO | WO03103835 | * | 6/2003 |
| WO | WO 03/071335 | | 8/2003 |
| WO | WO 03/083447 | | 10/2003 |
| WO | WO 03/103835 | | 12/2003 |

OTHER PUBLICATIONS

U.S. Appl. No. 10/094,093, filed Mar. 8, 2002, Eggleton et al.
U.S. Appl. No. 10/096,199, filed Mar. 12, 2002, Chandross et al.
U.S. Appl. No. 10/098,286, filed Mar. 15, 2002, Chen et al.
U.S. Appl. No. 10/135,973, filed Apr. 30, 2002, Z Bao et al.
U.S. Appl. No. 10/139,124, filed May 3, 2002, Kroupenkine et al.
U.S. Appl. No. 10/231,614, filed Aug. 30, 2002, Kroupenkine et al.
U.S. Appl. No. 10/321,027, filed Dec. 17, 2002, Reichmanis et al.
U.S. Appl. No. 10/83,150, filed Mar. 6, 2003, Chen et al.
U.S. Appl. No. 10/402,046, filed Mar. 28, 2003, Aizenberg et al.
U.S. Appl. No. 10/403,159, filed Mar. 31, 2003, Kornblit et al.
U.S. Appl. No. 10/631,996, filed Jul. 31, 2003, Aizenberg et al.
U.S. Appl. No. 10/637,837, filed Aug. 8, 2003, Davis et al.
U.S. Appl. No. 10/649,285, filed Aug. 27, 2003, Kornblit et al.
U.S. Appl. No. 10/674,448, filed Sep. 30, 2003, Hodes et al.
U.S. Appl. No. 10/716,084, filed Nov. 18, 2003, Kroupenkine et al.
U.S. Appl. No. 10/798,064, filed Mar. 11, 2004, Arney et al.
U.S. Appl. No. 10/803,565, filed Mar. 18, 2004, Hodes et al.
U.S. Appl. No. 10/803,576, filed Mar. 18, 2004, Kroupenkine et al.
U.S. Appl. No. 10/803,641, filed Mar. 18, 2004, Hodes et al.
U.S. Appl. No. 10/806,543, filed Mar. 23, 2004, Arney et al.
U.S. Appl. No. 10/810,774, filed Mar. 26, 2004, Krouopenkine et al.
U.S. Appl. No. 10/816,569, filed Apr. 1, 2004, Gasparyan et al.
Washizu, Masao, "Electrostatic Actuation of Liquid Droplets for Microreactor Applications," IEEE Transactions on Industry Applications, vol. 34, No. 4, Jul./Aug. 1998, pp. 732-737.
Schilling, Andreas et al., Surface Profiles of Reflow Microlenses Under the Influence of Surface Tension and Gravity, Opt. Eng. (39(8) pp. 2171-2176, Society of Photo-Optical Instrumentation Engineers, Aug. 2000.
Danzerbrink, R. et al., "Deposition of Micropatterned Coating Using an Ink-Jet Technique," Thin Solid Films 351, pp. 115-118, Elsevier Science S.A. (1999).
Feng, Chuan Liang et al., "Reversible Wettability of Photoresponsive Flourine-Containing Azobenzene Polymer in Langmuir-Blodgett Films," Lengmuir vol. 17, No. 15, 2001, pp. 4593-4597, American Chemical Society, published on Web. Jun. 22, 2001.
Ichimura, Kunihiro et al., "Light-Driven Motion of Liquids on a Photoresponsive Surface." Science. vol. 288. Jun. 2, 2000. pp. 1624-1626.
Commander, L.G. et al., "Variable Focal Length Microlenses," Optics Communications 177. Apr. 15, 2000. pp. 157-170.
Aizenberg, J., et al., "Calcitic microlenses as part of the photoreceptor system in brittlestars." Nature. vol. 412. pp. 819-822. Aug. 23, 2001.
English language translation of abstract for German Patent Document: DE 19623270 from European Patent Office database, esp@cenet.com, (1998), 1 page.
Tuberfield, A.J., "Photonic Crystals Made by Holographic Lithography," MRS. Bulletin. Aug. 2001. pp. 632-636.
Campbell, M., et al., "Fabrication of Photonic Crystals For The Visible Spectrum by Holographic Lithography," Nature, vol. 404, Mar. 2, 2000, pp. 53-56.
Ho, K.M., et al., "Existence Of A Photonic Gap In Periodic Dielectric Structures," Physical Review Letters, vol. 65, No. 25, Dec. 17, 1990, pp. 3152-3155.
Ozbay, E., et al., "Measurement Of A Three-Dimensional Photonic Band Gap in A Crystal Structure Made Of Dielectric Rods," Physical Review B, vol. 50, No. 3, Jul. 15, 1994, pp. 1945-1948.

Tuberfield, A., "Photonic Crystals Made By Holographic Lithography," Abstract from Symposium K, Microphotonics-Materials, Phyisics, and Applications, Nov. 26-29, 2001, 1 page.
Shoji, S., et al., "Photofabrication Of Three-Dimensional Photonlc Crystals By Multibeam Laser Interference Into A Photopolymarizable Resin," Applied Physics Letters, vol. 76, No. 19, May 8, 2000, pp. 2668-2670.
Sundararajan, N., et al., "Supercritical CO2 Processing for Submicron Imaging of Fluoropolymers," Chemistry of Materials, vol. 12, No. 1, Jan. 2000, pp. 41-48.
Kresge, C.T., et al: "Ordered mesoporous molecular sievas synthesized by a liquid-crystal template mechanism" Nature, vol. 359, Oct. 1992, pp. 710-712.
Tanev, Peter T., et al: "A Neutral Templating Route to Mesaporous Molecular Sieves." Science. vol. 267. Feb. 1995. pp. 855-867.
Huo, Q. et al: "Generalized synthesis of periodic surfactant/inorganic composite materials." Nature. vol. 368. Mar. 1994. pp. 317-321.
Sanchez, C., et al: "Design and Properties of Hybrid Organic-Inorganic Nanocomposites for Photonics," MRS Bulletin, May 2001, pp. 377-387.
Yang, P., et al: "Hierarchically Ordered Oxides," Science, vol. 282, Dec. 1998, pp. 2244-2246. Templln, M. et al: "Organically Modified Aluminosilicate Mesostructures from Block Copolymer Phases," Science, vol. 278, Dec. 1997, pp. 1795-1798.
Raman, N.K., et al: "Template-Based Approaches to the Preparation of Amorphous Nanoporous Silicas," Chemical Matter, vol. 8, Feb. 1996, pp. 1682-1701.
Yang, P., et al: "Block Copolymer Templating Synthesis of Mesoporous Metal Oxides with Large Ordering Lengths and Semicrystalline Framework," Chemical Matter, vol. 11, 1999, pp. 2813-2826.
Brinker, C.J., et al., "Evaporation-Induced Self-Assembly: Nanostructures Made Easy**" Advanced Materials. vol. 11. 1999. pp. 579-585.
Lee, Y-J., Braun, P.V., "Tunable Inverse Opal Hydrogel pH Sensors," Adv. Mater. 2003, 15. No. 7-8. Apr. 17, 2003. pp. 563-566.
Arsenault, A.C., et al., "A Polychromic, Fast Response Metallopolymer Gel Photonic Crystal with Solvant and Redox Tunability: A Step Towards Photonic Ink (P-Ink)," Adv. Mater. 2003, 15, No. 6, Mar. 17, 2003, pp. 503-507.
Zhang, S., et al., "Materials and techniques for electrochemical biosensor design and construction," Biosensors & Bioelectronics 15, (2000), pp. 273-282.
Wu, H., et al., "Reduction Photolithography Using Microlens Arrays: Applications in Gray Scale Photolithography," Analytical Chemistry, vol. 74, No. 14, Jul. 15, 2002, pp. 3267-3273.
Leister Microsystems, leaflet by Leister Microsystems entitled, "Micro-optics—Imagine the Future of Light." Sep. 2000, 4 pages.
Stokes, D.L., et al., "Detection of *E. coli* using a microfluidics-based Antibody Biochip detection systems," Fresenius, J. Anal Chem (2001) 369, pp. 295-301.
Jahns, J., et al., "Microoptics for biomedical applications," American Biotechnology Laboratory. No. 18. Oct. 2000. pp. 52 and 54.
Campbell, D.J., et al., "Replication and Compression of Bulk and Surface Structures with Pholydimethylsiloxane Elastomer," Journal of Chemical Education, vol. 75, No. 4, Apr. 1999, pp. 537-541.
Kruk, M., et al., "Mesoporous Silicate-Surfactant Composites with Hydrophobic Surfaces Tailored Pore Sizes"; Journal of Physical Chemistry 106 B (2002) pp. 10096-10101.
Thrush, E., et al., "Integrated semiconductor fluorescent detection system for biochip and biomedical applications," IEEE-EMBS Special Topic Conference on Microtechnologies in Medicine & Biology. May 2002. pp. 374-379.
Avgeropoulos, et al., "Synthesis and Morphological Behavior of Silicon-Containing Triblock Copolymers for Nanostructure Applications," Chem. Mater. 1998, 10, pp. 2109-2115.
Chan, Vanessa A-H., et al., "Ordered Bicontinuous Nanoporous and Nanorelief Ceramic Films from Self-Assembling Polymer Precursors," Science, Nov. 26, 1999, vol. 286, pp. 1716-1719.
Shishido, A., et al., "Direct fabrication of two-dimensional titania arrays using interference photolithography," Applied Phyiscal Letters, vol. 79, No. 20, Nov. 12, 2001, pp. 3332-3334.

Young, "Organic-Inorganic Monomers," accessed at http://www.psrc.usm.edu/mauritz/nano2.html. Jul. 8, 2002.

Yang, et al., "Creating Periodic Three-Dimensional Structures by Multibeam Interference of Visible Laser," Chemistry of Materials, vol. 14, No. 7, Jul. 2002, pp. 2831-2833.

Vlasov et al., "On-Chip Netural Assembly of Silicon Photonic Bandgap Crystals." Nature. vol. 414. Nov. 15, 2001. pp. 289-293.

Baney, et al., "Silsesquioxanes," American Chemical Society, 1995, pp. 1409-1430.

The Wittman Company, "Carbon Dioxide," published online at http://www.witteman.com/co2.htm. Dec. 4. 2002. 2 pages.

"Sol-Gel Chemistry," published online at http://www.sol-gel.com/chemi.htm, Dec. 9, 2002. 2 pages.

Abbot, N. L., et al., "Potential-Dependent Wetting of Aqueous Solutions on Self-Assembled Monolayers Formed from 15-(Ferrocenylcarbonyl) pentadecanethiol on Gold," Langmuir 1994, American Chemical Society, vol. 10, pp. 1493-1497.

Abbot, N. L., et al. "Potential-Dependent Wetting of Aqubous Solutions on Self-Assembled Monolayers Formed from 15-(Ferrocenylcarbonyl) Pentadecaneithiol on Gold," Langmuir 1994, American Chemical Society, vol. 10, pp. 1493-1497.

Kim, et al, "Nanostructured Surfaces for Dramatic Reduction of Flow Resistance in Droplet-Based Microfluidics." IEEE. pp. 479-482 (2002).

E.W. Becker, et al., "Fabrication of microstructures with high aspect ratios and great structural heights by synchrotron radiation lithography, galvanoforming, and plastic moulding (LIGA process)", Microelectronic Engineering Elsevier Publishers BV, Amsterdam, NL, vol. 4, pp. 1 (May 1, 1986) pp. 35-56.

Surface Energy Material (dynes/cm), ACCUDYNETE, "Solid Surface Energies," accessed at http://www.accudynetest.com/surface_energy_materials.html, Jul. 27, 2005 (3 pages).

eFunda: General Information on Element Silicon, accessed at http://www.efunda.com/materials/elements/element_info.cfm?Element_ID=Si, Aug. 10, 2005 (8 pages).

Bhardwaj, et al., "Advances in High Rate Silicon and Oxide Etching using ICP", STS Ltd., Imperial Park, Newport, UK NP10 89UJ (6 pags).

Templin, et al., "Organically Modified Aluminosilicate Mesostructrures from block Copolymer Phases", www.sciencemag.org, Science, vol. 278, Dec. 5, 1997, pp. 1795-1798.

Four (4) European Search Reports each dated Sep. 15, 2004.

Krupenkin, et al.; From rolling ball to complete wetting: the dynamic tuning of liquids on nanostructured surfaces; Langmuir 2004, 20, pp. 3824-3827.

Krupenkin, et al.; From rolling ball to complete wetting: the dynamic tuning of liquids on nanostructured surfaces; Abstract Y22.006; Abstracts, meeting of the American Physical Society in Montreal, Canada, Mar. 22-26, 2004, 4 Pages.

Bell Labs scientists discover technique to control fluids using specially fabricated silicon "nanograss"; Lucent Technologies, press release Mar. 12, 2004. 3 Pages (no. longer available on Lucent's press archive, but available through the Internet Archive).

Taylor, J. Ashley, et al.; Nanotech Makes Liquids Manageable; Energy Optimization News, May 1, 2004, 1 Page.

Tunable Surfaces; Physics News 678, Mar. 26, 2004 (American Institute of Physics), 2 Pages.

Weiss, Peter; Super-repellent surface switches on and off; Science News, Apr. 24, 2004, vol. 165, Issue 17, p. 270 (2 pages).

Gonsalves, Antone, Bell Labs Invention Could Mean Cooler Chips, Techweb Network, Mar. 12, 2004, 2 Pages.

Chang, Kenneth, 'Nanograss' Turns Sticky to Slippery in an Instant, The New York Times, Mar. 16, 2004, 2 Pages.

KrupenKin, T., et al., Tunable liquid microlens, Applied Physics Letters, vol. 82, No. 3, Jan. 20, 2003, pp. 316-318.

Pamula, Vamsee K., et al., Cooling of Integrated Circuits Using Droplet-Based Microfluidics, Proceedings of the 13th ACM Great Lakes symposium on VLSI, Washington DC, Apr. 28-29, 2003, pp. 84-87 (4 Pages).

Oprins, H., et al., On-Chip Liquid Cooling with Integrated Pump Technology, 21st IEEE Semi-Therm Symposium, San Jose, CA, Mar. 15-16, 2005, 7 Pages.

Krupenkin, Tom, et al., Electrically Tunable Superhydrophobic Nanostructured Surfaces, Bell Labs Technical Journal 10(3), pp. 161-170.

\* cited by examiner

LOW ADSORPTION SURFACE

TECHNICAL FIELD OF THE INVENTION

The present invention is directed, in general, to a device and method for reducing the adsorption of samples on a surface of the device.

BACKGROUND OF THE INVENTION

One problem encountered when handling small fluid sample volumes in devices is the non-specific adsorption of the sample on surfaces of the device. The term sample as used herein is defined as any fluid comprising a material that is the subject of an analysis. In some cases, the sample comprises a material dissolved or suspended in a liquid. In other cases, the sample comprises liquid, or mixture of liquids, that is itself the material subject to analysis. Sample adsorption can be problematic in analytical devices that transport and analyze small volumes. Substantial amounts of sample, sometimes the entire sample, can adhere to a surface of the device while being transported to a particular location in the device designated for analysis. This is especially problematic when handling biological samples comprising materials such as proteins or DNA, although similar concerns exist for the analysis of non-biological samples. In other cases the fluid in which the material of interest is dissolved or suspended can adhere to device surfaces, thereby undesirably altering the concentration of material in the sample.

Undesired sample adsorption can substantially reduce the amount of sample delivered to the analytical site of the device, thereby reducing the sensitivity of the analysis. Moreover, if the sample later de-adsorbs from device surfaces it can then become a contaminant in subsequent analyses, causing a reduction in the accuracy of the analysis. Additionally, the adsorbed sample can interact with subsequent samples, thus further altering the concentration or composition of the subsequent sample and therefore reducing the sensitivity or accuracy of the analysis.

Embodiments of the present invention overcome these problems by providing a device that reduces the non-specific adsorption of sample on a surface of the device, as well as by providing methods of using and making such a device.

SUMMARY OF THE INVENTION

To address the above-discussed deficiencies, one embodiment of the present invention is a device. The device comprises an analytical sample substrate having at least one region that comprises a plurality of sample-support-structures. Each of the sample-support-structures has at least one dimension of about 1 millimeter or less. A sum of areas of contact surfaces of the sample-support-structures is substantially less than a total area of the region. The contact surfaces define a prescribed sample path to an analytical depot located on the analytical sample substrate.

Another embodiment is a method of use. The method comprises placing a sample on an analytical sample substrate having at least one region that comprises a plurality of the above-described sample-support-structures. The method further includes moving the sample over a prescribed sample path defined by the contact surfaces to an analytical depot.

Yet another embodiment comprises a method of manufacturing a device. The method comprises forming a plurality of the above-described sample-support-structures on a region of an analytical substrate and forming an analytical depot located on the analytical sample substrate and at a terminus of a prescribed sample path

BRIEF DESCRIPTION OF THE DRAWINGS

The invention is best understood from the following detailed description, when read with the accompanying figures. Various features may not be drawn to scale and may be arbitrarily increased or reduced for clarity of discussion. Reference is now made to the following descriptions taken in conjunction with the accompanying drawings, in which.

DETAILED DESCRIPTION

The present invention recognizes for the first time that nanostructures or microstructures can provide a novel result-effective variable for minimizing the adsorption of samples on a surface of a device. The term nanostructure as used herein refers to a predefined raised feature on a surface that has at least one dimension that is about 1 micron or less. The term microstructure as used herein refers to a predefined raised feature on a surface that has at least one dimension that is about 1 millimeter or less. Exemplary devices of the present invention have sample-support-structures comprising nanostructures or microstructures. The sample-support-structures provide a smaller area to interface with a sample than a conventional device having a planar surface. Because there is a smaller liquid-solid interface available for sample adsorption, a smaller amount of sample is adsorbed as compared to conventional device surfaces.

Figure 1:
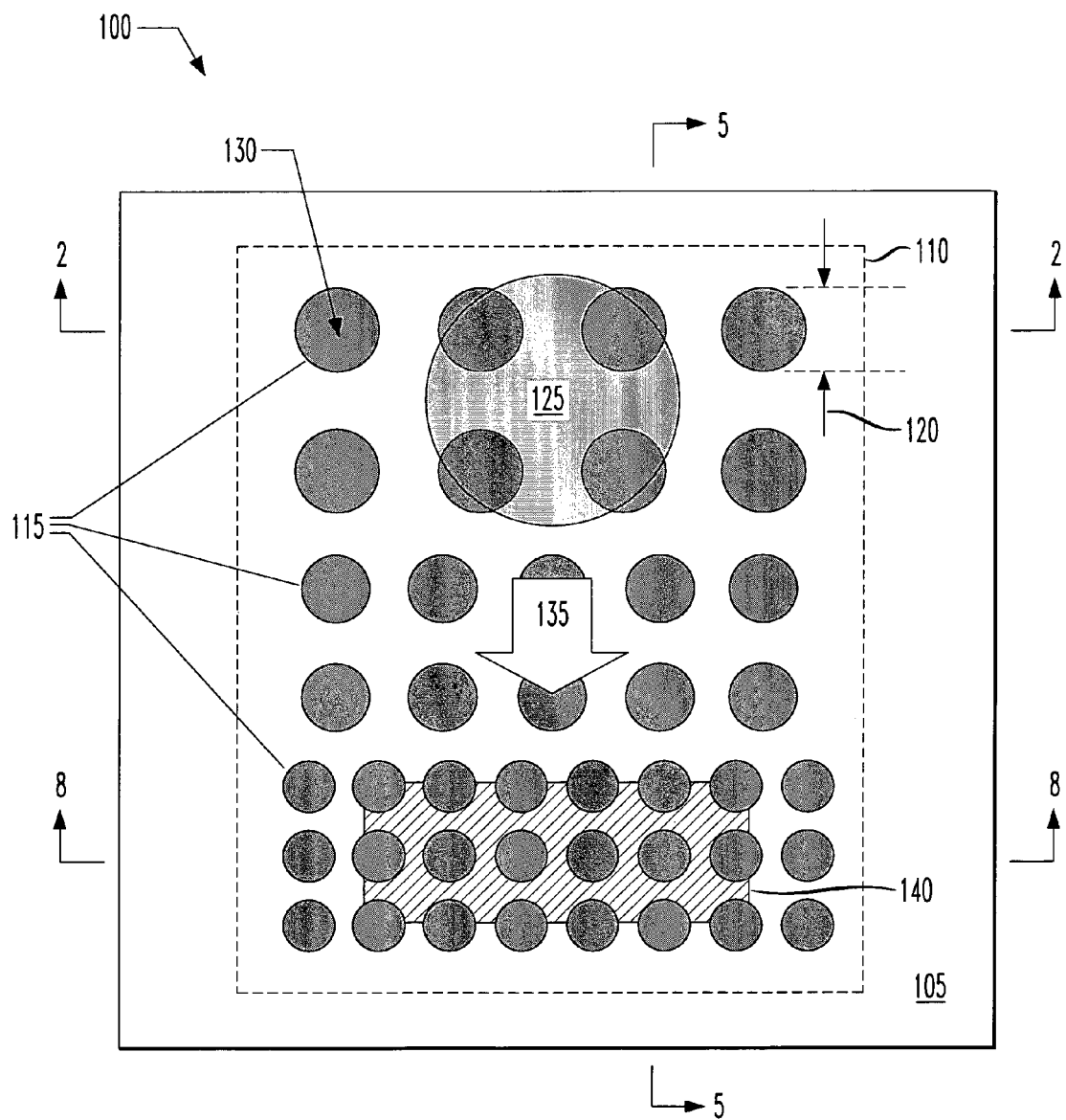
FIG. 1 presents a plan view of an exemplary device 100 to illustrate certain features of the present invention.

One embodiment of the present invention is a device. Some preferred embodiments of the device comprise a mobile diagnostic device such as a lab-on-chip. FIG. 1 presents a plan view of an exemplary device 100 to illustrate certain features of the present invention. The device 100 comprises an analytical sample substrate 105 having at least one region 110 that comprises a plurality of sample-support-structures 115. Each of the sample-support-structures 115 have at least one dimension 120 of about 1 millimeter or less, and in some embodiments, about 1 micron or less. That is, the sample-support-structures 115 can comprise microstructures, nanostructures, or both. To provide a small liquid-solid interface with a sample 125, the sample-support-structures 115 are configured to provide a sum of areas of contact surfaces 130 of the sample-support-structures 115 that is substantially less than a total area of the region 110.

Additionally, the contact surfaces 130 define a prescribed sample path 135 to an analytical depot 140 located on the analytical sample substrate 105. The analytical depot 140 comprises any conventional structures or materials to facilitate the identification or to characterize some property of the sample 125. For example, the analytical depot 140 can comprise a reagent configured to interact with the sample 125, thereby identifying a property of the sample. As another example, the analytical depot 140 can comprise an organic field-effect transistor (OFET) configured to generate an electrical signal when it comes in contact with a particular type of DNA, protein or other material of interest dissolved or suspended in the sample 125.

As noted above, the sample-support-structures 115 are configured so that the sum of areas of contact surfaces 130 of the sample-support-structures 115 is substantially less than a total area of the region 110. For example, in some preferred embodiments of the device 100, the sum of areas of contact surfaces 130 is about 10 percent or less than a total area of the region 110. In other preferred embodiments, the sum of areas of contact surfaces 130 is about 1 percent or less than a total area of the region 110. In still other preferred embodiments, the sum of areas of contact surfaces 130 is about 0.1 percent or less than a total area of the region 110.

Figure 2:
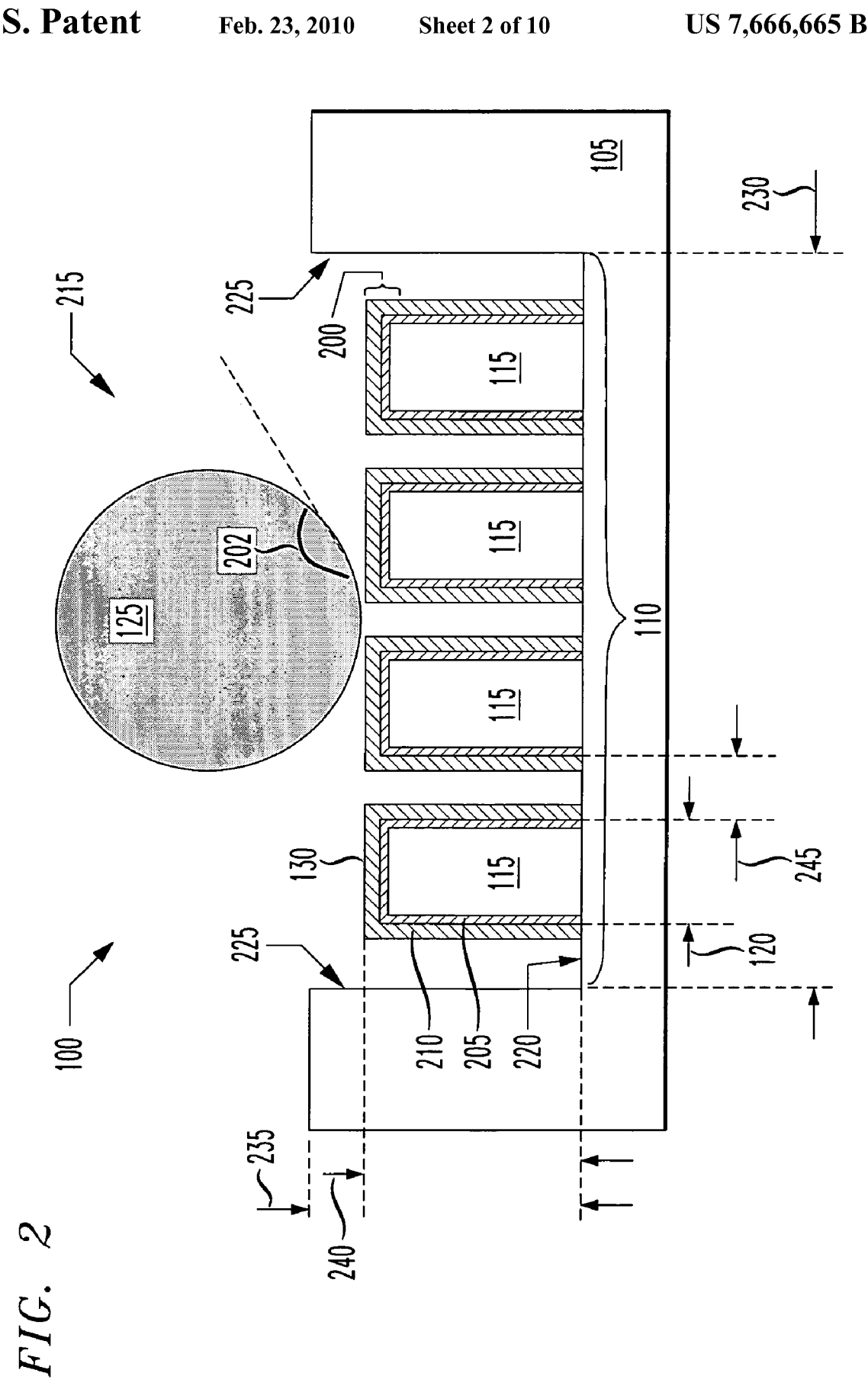
FIG. 2, shows a cross-sectional view through the device presented in FIG. 1.

Shown in FIG. 2 is a cross-sectional view through the device 100 presented in FIG. 1, through view line 2-2. As illustrated in FIG. 2, the contact surface 130 corresponds to that portion of the sample-support-structure 115 that the sample 125 touches. In some preferred embodiments, the sample-support-structures 115 are configured to cooperatively support the sample 125 so that the contact surface 130 corresponds to the upper-most exterior portion 200 (e.g., uppermost 1 to 10 percent) of each structure 115. For example, consider an embodiment where the sample 125 comprises a droplet of water. The sample-support-structures 115 can be configured so that the sample 125 forms a contact angle 202 of about 140 degrees or higher. Consequently only a small portion of the sample-support-structures 115 is touched by the sample 125.

As further illustrated in FIG. 2, in some cases, it is desirable for the sample-support-structures 115 to include a coating 205 comprising low surface energy and electrically insulating materials. The low surface energy material facilitates obtaining the above-described contact angle 202. The term low surface energy material as used herein refers to a material having a surface energy of about 22 dyne/cm (about $22 \times 10^{-5}$ N/cm) or less. Those of ordinary skill in the art would be familiar with the methods to measure the surface energy of materials. In embodiments where a voltage is applied to the device 100, either to induce sample movement, penetration, or both, the insulating material advantageously provides electrical insulation between the sample 125 and fluid-support-structures 115, both of which are conductive in this case.

In some cases the coating 205 comprises a single material, such as Cytop® (Asahi Glass Company, Limited Corp. Tokyo, Japan), a fluoropolymer that is both an electrical insulator and low surface energy material. In other cases, the coating can comprise separate layers of insulating material and low surface energy material. For example, the coating can comprise a layer of a dielectric material, such as silicon oxide, and a layer of a low-surface-energy material, such as polytetrafluoroethylene.

As also illustrated in FIG. 2, in some instances, it is desirable to further reduce sample adsorption by coating the sample-support-structures 115 with an anti-adsorption layer 210. In the embodiment presented in FIG. 2, each of the sample-support-structures 115 is coated with an anti-adsorbing layer 210. A conformal coating is desirable so that the sample-support-structures 115 substantially retain their dimensions. For example, the anti-adsorption layer 210-coated sample-support-structures 115 in FIG. 2 still have at least one dimension 120 that is about 1 millimeter or less, or in some cases about 1 micron or less.

One of ordinary skill in the art would be familiar with suitable anti-adsorption materials and how to adjust the composition of the anti-adsorption layer 210 depending upon the nature of the sample 125. For instance, consider when the sample 125 comprises a material of interest that is a protein. In this case, some preferred embodiments of the anti-adsorbing layer 210 comprise polyethylene glycol (PEG) or other material that adsorbs the same or lesser amount of protein than a PEG layer per unit area. In certain preferred embodiments, the anti-adsorbing layer 210 adsorbs less than a quarter of an amount of a test protein (e.g., insulin or BSA), and more preferably less than 10%, per unit area, as compared to a surface not having the adsorbing layer 210-coated sample-support-structures 115.

In some cases, to retain the above-described desirable features of the coating 205 comprising a low surface energy material, the anti-adsorption layer 210 comprises a combination of anti-adsorption and low surface energy material. For example, in some embodiments, the coating 205 comprises an electrical insulator such as silicon oxide, and the anti-adsorption layer 210 comprises PEG plus a low surface energy fluoropolymer. One of ordinary skill in the art would understand how to adjust the proportions of anti-adsorption and low surface energy material in the layer 210 to ensure that the contact angle 202 is above about 90 degrees, and more preferably about 140 degrees or higher.

In some preferred embodiments, to minimize sample adsorption while moving along on the prescribed path 135, the device 100 is configured so that the sample 125 substantially touches only the contact surface 130, and the sample 125 is separated from any other surfaces of the device 100. In some cases, for example, at least about 90 percent, and more preferably greater than 99 percent, of the solid surfaces that the sample 125 touches corresponds to the contact surface 130 of the sample-support-structures 115.

In some cases, the sample 125 is separated from other surfaces of the device 100 by providing the prescribed path 135 on a flat surface of the substrate 105. In other cases, however, such as illustrated in FIG. 2, the prescribed sample path 135 is in a channel 215. In such embodiments, the region 110 having sample-support-structures 115 comprises an interior surface of the channel 215. For the device 100 illustrated in FIG. 2, the region 110 comprises a floor 220 of the channel 215. Of course, in other embodiments of the device 100, there could be additional regions, such as the channel walls 225, that have sample-support-structures 115. In some cases, in addition to the sample-support-structures 115, the channel floor 220 and walls 225 are also conformally coated with the anti-adsorbing layer 210.

In some cases, the channel 215 is a microfluidic channel configured to transport a continuous or intermittent flow of sample 125. For the purposes of the present invention, a microfluidic channel is defined as a channel having at least one dimension that is about 1 millimeter or less. For instance, both the width 230 and height 235 of the channel 215 can be about 1 millimeter or less. Having at least one interior surface of the channel 230 covered with the sample-support-structures 115 allows extremely small channels to be used. For example, in some preferred embodiments, the channel 215 has a width 230 and height 235 each ranging from about 10 to about 100 microns. Such small-dimensioned channels are difficult to realize in conventional channels having conventional surfaces, because an unacceptably high pressure would have to be applied to force fluid through the channel. In contrast, the sample-support-structures 115 provide a surface having a very low flow resistance, thereby allowing small-dimensioned channels to be used.

A problem encountered in conventional channels is that the sample flows more slowly at the wall than at the center of the channel, due to the increased flow resistance at the walls of the channel. Different flow rates across the width of a channel can cause the sample to be spread out over a length of the channel, thereby diluting the sample and increasing the period to deliver the total amount sample to a desired location.

Dilution, in turn, can reduce the sensitivity of the analysis and the longer delivery time can increase the minimum interval between successive runs of samples through a device having such a channel.

Embodiments of the device 100 overcome this problem by reducing the flow resistance encountered at interior surfaces of the channel 215. Flow resistance is reduced by providing at least one interior surface, such as the floor 220 or walls 225 of the channel 215, or both, that are covered with the sample-support-structures 115. A reduced flow resistance of the this interior surface beneficially lowers the pressure drop through the channel 215 and allows a more uniform flow of sample 125 across the width 230 or height 235 of the channel 215. Consequently the sample 125 is less prone to dilution and the sample 125 gets delivered to the analytical depot 140 over a shorter interval. In some preferred embodiments, the floor 220 or walls 225 of the channel 215 also can have the above-discussed coating 205 of the electrical insulating and low surface energy materials, and the anti-absorption layer 210.

The extent of reduction in flow resistance encountered at the interior surface of the channel 215 and the improved uniformity of sample flow can be quantified by a slip length. In some preferred embodiments of the device 100, the channel 215 has a slip length that is at least about 10 percent of a width 230 of the channel 215. The term slip length as used herein refers to a theoretical diameter or width outside the channel 215 where liquid velocity extrapolates to zero. In other words, the slip length characterizes how much wider or higher the channel 215 would have to be to make the fluid velocity go to zero at the interior surfaces of the channel 215. Those skilled in the art would be familiar with the methods used to measure slip length.

Embodiments of the sample-support-structures can have any number of different shapes and spacing relative to each other, so long as they provide a small area of contact surface and meet the dimensional requirements as discussed above. The requirement that sample-support-structures each have at least one dimension of about 1 millimeter or less is essential to ensure that a sample will be located on the uppermost portion of the structure and hence will provide the requisite small contact surface relative to the region on which the sample-support-structures are located.

In some instances, the sample-support-structures are laterally separated from each other. For example, the sample-support-structures 115 depicted in FIGS. 1 and 2 are post-shaped, and more specifically, cylindrically-shaped posts. The term post as used herein, includes any structures having cylindrical, square, rectangular or other shapes. For the some embodiments configured as presented in FIGS. 1 and 2, the one dimension that is about 1 millimeter or less is a lateral thickness 120 or diameter of the post. In certain preferred embodiments, each of the sample-support-structures 115 have a uniform height 240 ranging from about 1 to about 10 microns and a diameter 120 of about 1 micron or less.

In some cases, it is advantageous to arrange the sample-support-structures 115 into a two-dimensional array. In other cases, the sample-support-structures 115 have a uniform spacing 245 apart from each other. In certain embodiments, for example, the spacing 245 between the sample-support-structures 115 is a uniform distance ranging from about 1 to about 10 microns. However, in other cases, the spacing 245 can be non-uniform. For instance, in some cases, as further discussed below, it is desirable to progressively decrease the spacing 245 between sample-support-structures 115 along the prescribed path to the analytical depot 140. For example, the spacing can be progressively decreased from about 10 microns to about 1 micron.

The size and spacing of the sample-support-structures can be altered to adjust a sum of the areas of the contact surfaces 130, and therefore the extent of adsorption of the sample 125 on the device 100. For example, consider embodiments where the support structures 115 are configured as posts having a diameter 120 of about 300 nm and spacing 245 of about 4 microns. In such embodiments the sum of contact surface areas is about 1% or less of the total area of the region 110. In other embodiments, where sample-support-structures 115 are configured as posts having a diameter 120 of about 100 nm and spacing 245 of about 4 microns, the sum of contact surface areas is about 0.1% or less of the total area of the region 110.

Figure 3:
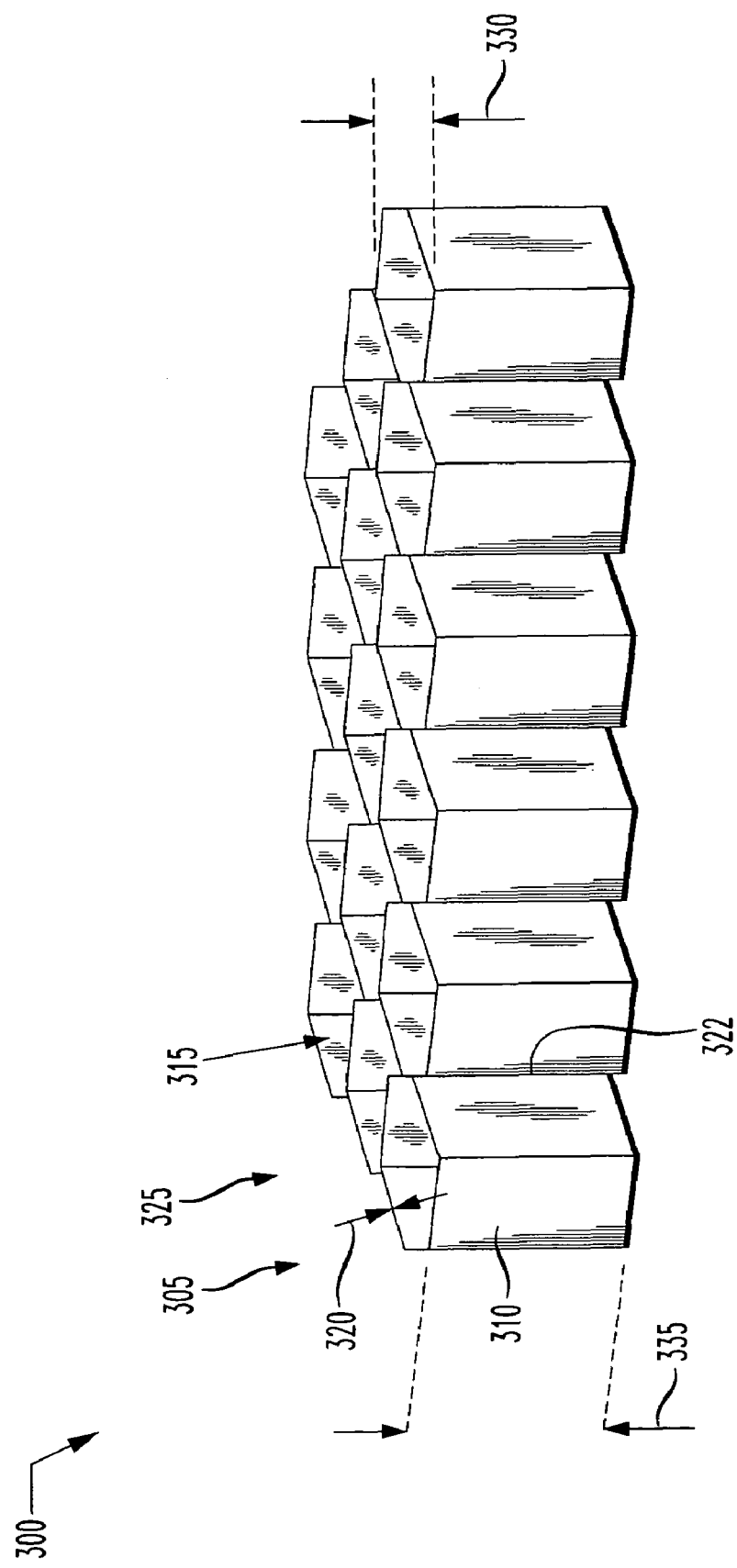
FIG. 3 presents a perspective view of sample-support-structures that comprises one or more cell.

In other instances, the sample-support-structures are laterally connected to each other. For example, FIG. 3 presents a perspective view of sample-support-structures 300 that comprise one or more cells 305. The term cell 305 as used herein refers to a structure having walls 310 that enclose an open area 315 on all sides except for the side over which a sample could be disposed. In such embodiments, the one dimension that is about 1 micrometer or less is a lateral thickness 320 of walls 310 of the cell 305. As illustrated in FIG. 3, the sample-support-structures 300 are laterally connected to each other because the cell 305 shares at least one wall 322 with an adjacent cell 325. In certain preferred embodiments, a maximum lateral width 330 of each cell 305 is about 15 microns or less and a maximum height 335 of each cell wall is about 50 microns or less. For the embodiment shown in FIG. 3, each cell 305 has an open area 315 prescribed by a hexagonal shape. However in other embodiments of the cell 305, the open area 315 can be prescribed by circular, square, octagonal or other shapes.

Another aspect of the present invention is a method of use. FIGS. 4-7 present cross-section views of the exemplary device 100 shown in FIG. 1, through view line 5-5, at various stages of use. FIGS. 4-7 use the same reference numbers to depict analogous structures shown in FIGS. 1-2. However, any of the various embodiments of the devices of the present inventions discussed above and illustrated in FIGS. 1-3 could be used in the method.

Figure 4:
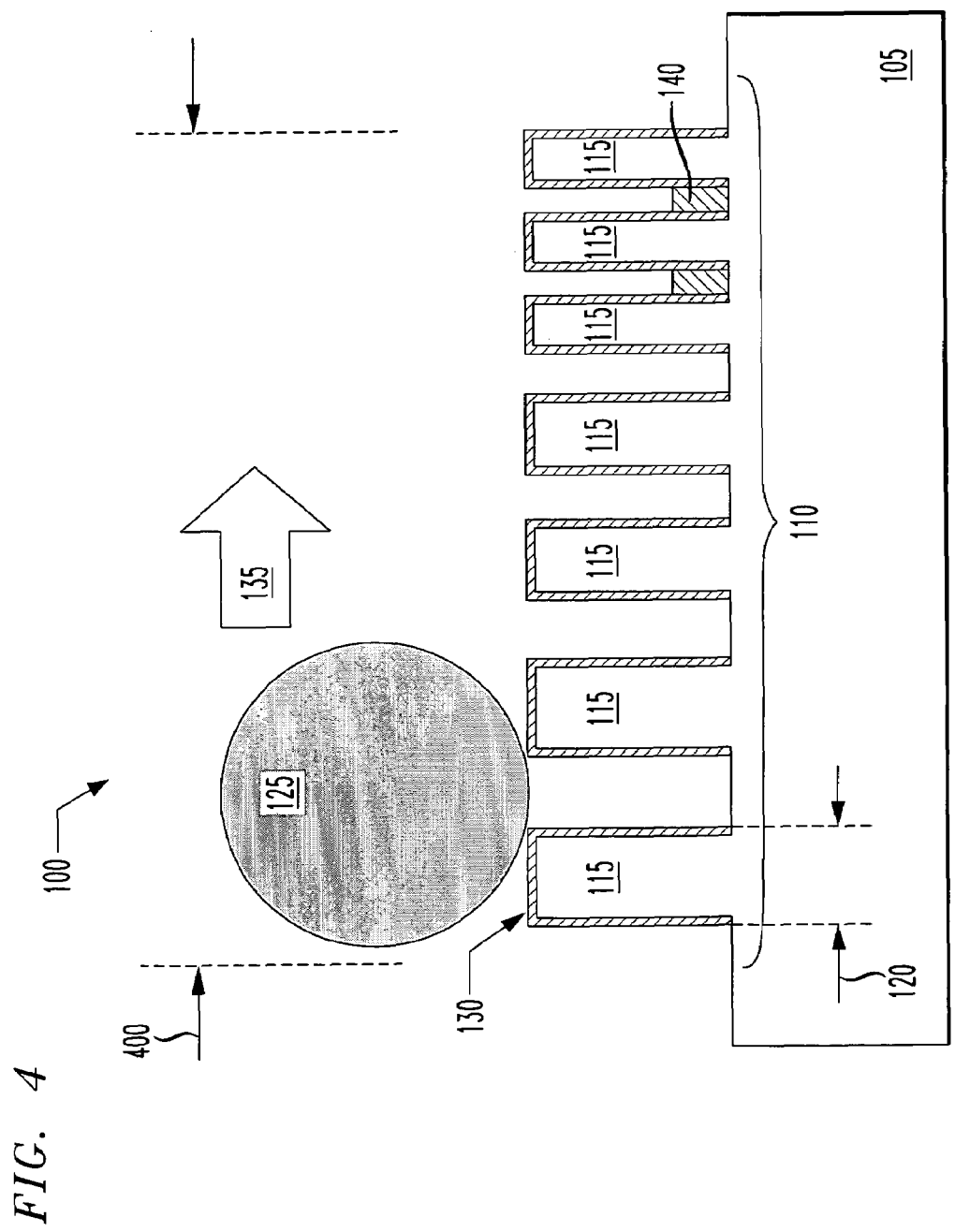
FIGS. 4-7 present cross-section views of the exemplary device shown in FIG. 1, at various stages of use.

Turning now to FIG. 4, while maintaining reference to FIGS. 1-2, illustrated is the device 100 after placing a sample 125 on an analytical sample substrate 105 having at least one region 110 that comprises a plurality of sample-support-structures 115. As with the above-discussed device embodiments, each of the sample-support-structures 115 has at least one dimension, in this case a width 120, that is about 1 millimeter or less, and in some cases, 1 micron or less. Additionally the sum of areas of the contact surfaces 130 of the sample-support-structures 115 is substantially less than a total area of the region 110.

In certain embodiments, the device 100 is configured so that a distance 400 to be traversed by the sample 125 over the prescribed sample path 135 to the analytical depot 140 can range from about 100 microns to about 1 cm. Preferably, substantially none of the sample 125 is adsorbed while traversing the prescribed sample path 135. For instance, in some cases, less than about 1 percent of the sample 125 adheres to the region 110 after the sample 125 traverses the prescribed sample path 135. In other cases, less than about 1 percent of a material suspended or dissolved in the sample 125, such as a protein, adheres to the region 110 after the sample 125 traverses the prescribed sample path 135.

While maintaining reference to FIGS. 1-2 and 4, FIG. 5 depicts the device 100 after moving the sample 125 over a prescribed sample path 135 defined by the contact surfaces 130 to an analytical depot 140 located on the analytical sample substrate 105. Numerous methods can be used to facilitate the movement of the sample 125 along the prescribed sample path 135. As already discussed, in some cases, the prescribed sample path is in a channel 215 (FIG. 2), and at least one interior surface of the channel 215 comprises a region 110 with sample-support-structures 115 thereon. In such cases, a pressure can be applied to force the sample 125 through the channel 215 and to the analytical depot 140. The prescribed sample path 135, however, does not need to be in a channel, and numerous other methods can be used to facilitate the movement of the sample 125.

Figure 5:
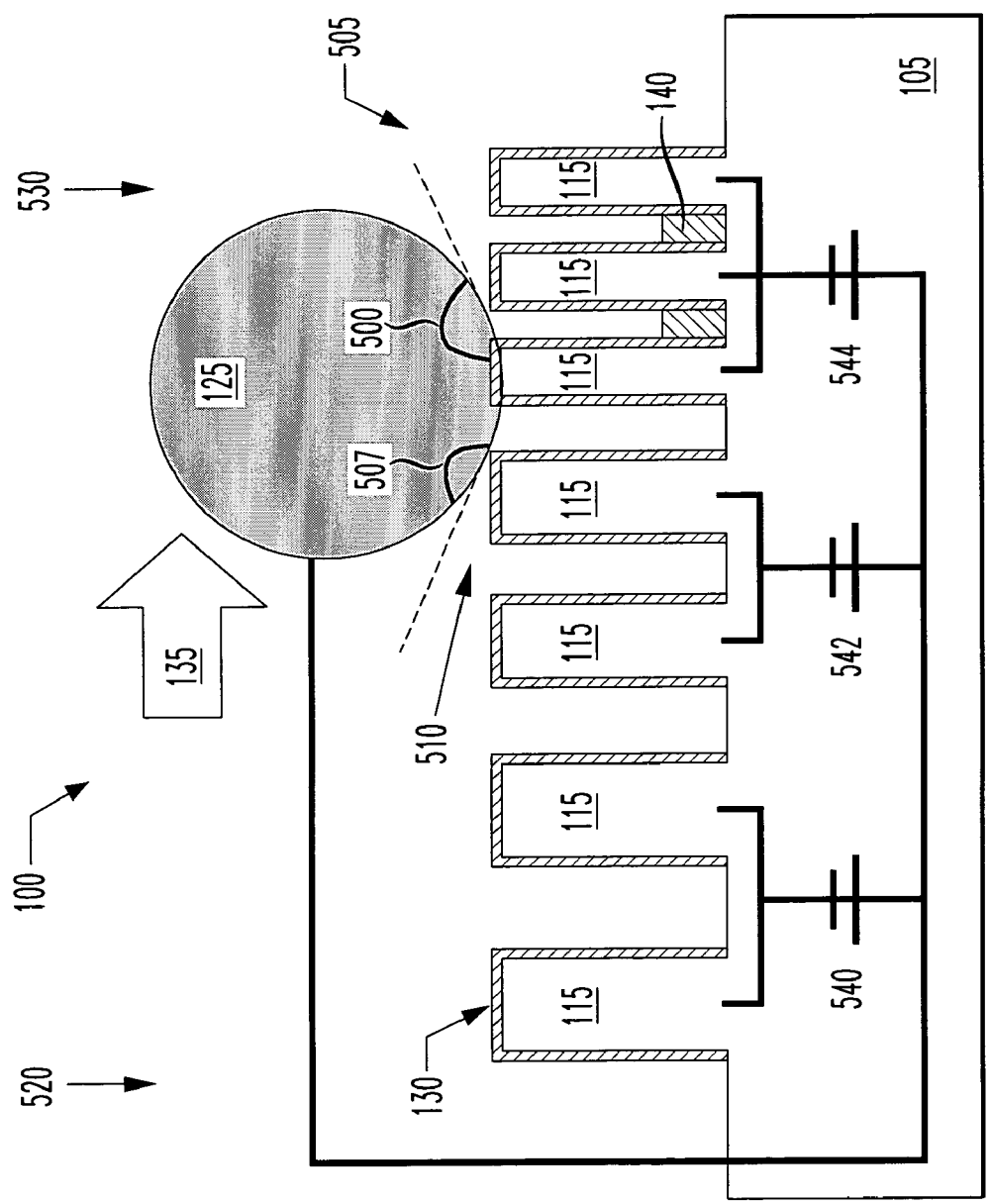

For example, movement can be facilitated by providing an increased area of contact surfaces 130 of the sample-support-structures 115 in a direction towards the analytical depot 140. As illustrated in FIG. 5, the area of contact surfaces 130 can be increased by increasing the density of sample-support-structures 115 (e.g., the number of structures 115 per unit area) in a direction of the prescribed sample path 135. Therefore, the total area of contact surfaces 130 progressively increases in a direction towards the analytical depot 140.

The increased area of contact surfaces 130 of the sample-support-structures 115 in a direction towards the analytical depot 140 is reflected by an asymmetry in the contact angle 500 of the sample 125. That is, the contact angle 500 of the sample 125 decreases as the total area of contact surfaces 130 increases. Consequently, the sample 125 moves along the path 135 because the sample 125 has a lower contact angle 500 at the leading edge 505 of the sample 125, i.e., the edge closest to the analytical depot 140, as compared to the contact angle 507 at the trailing edge 510.

As illustrated in FIG. 5, with continuing reference to FIG. 2, the density can be progressively increased by gradually decreasing the spacing 245 between structures 115 with a concurrent decrease the sample-support-structure's diameter 120. In other cases (not shown), the density can be increased by decreasing the spacing 245 between structures 115 while keeping the diameter 120 constant. In still other cases (not shown), the total area of contact surfaces 130 can be increased in a direction of the prescribed sample path 135 without increasing the density of structures 115, by increasing the diameter of the individual sample-support-structures 115 with a concurrent decrease in the spacing 245 between structures 115.

The extent of increase in the density the sample-support-structures 115 has to be balanced with the desire to keep the sum of areas of contact surfaces 130 less than the total area of the region 110. In some preferred embodiments, for example, the sum of areas of contact surfaces 130 ranges from about 0.1 percent of the total area of the region 110 at an initial point of sample application 520 to about 1 percent of the total area of the region 110, at a terminus 530 of the path 135. In other preferred embodiments, the sum of areas of contact surfaces 130 ranges from about 1 percent of the total area of the region 110 at an initial point of sample application 520 to about 10 percent of the total area of the region 110, at a terminus 530 of the path 135.

As another example, movement can also be facilitated by applying voltages 540, 542, 544 between the sample 125 and the sample-support-structures 115. In some cases, the voltages 540, 542, 544 are progressively increased in a direction towards the analytical depot 140. The contact angle 500 of the sample decreases as the voltage between the sample 125 and the sample-support-structures 115 increases. Similar to that discussed above, the sample 125 moves along the path 135 because the sample 125 has a lower contact angle 500 at the leading edge 505 of the sample 125, than the contact angle 507 at the trailing edge 510. Of course, the above-described methods of moving the sample 125 can be combined with each other or with other methods that would be readily apparent to those skilled in the art.

Figure 6:
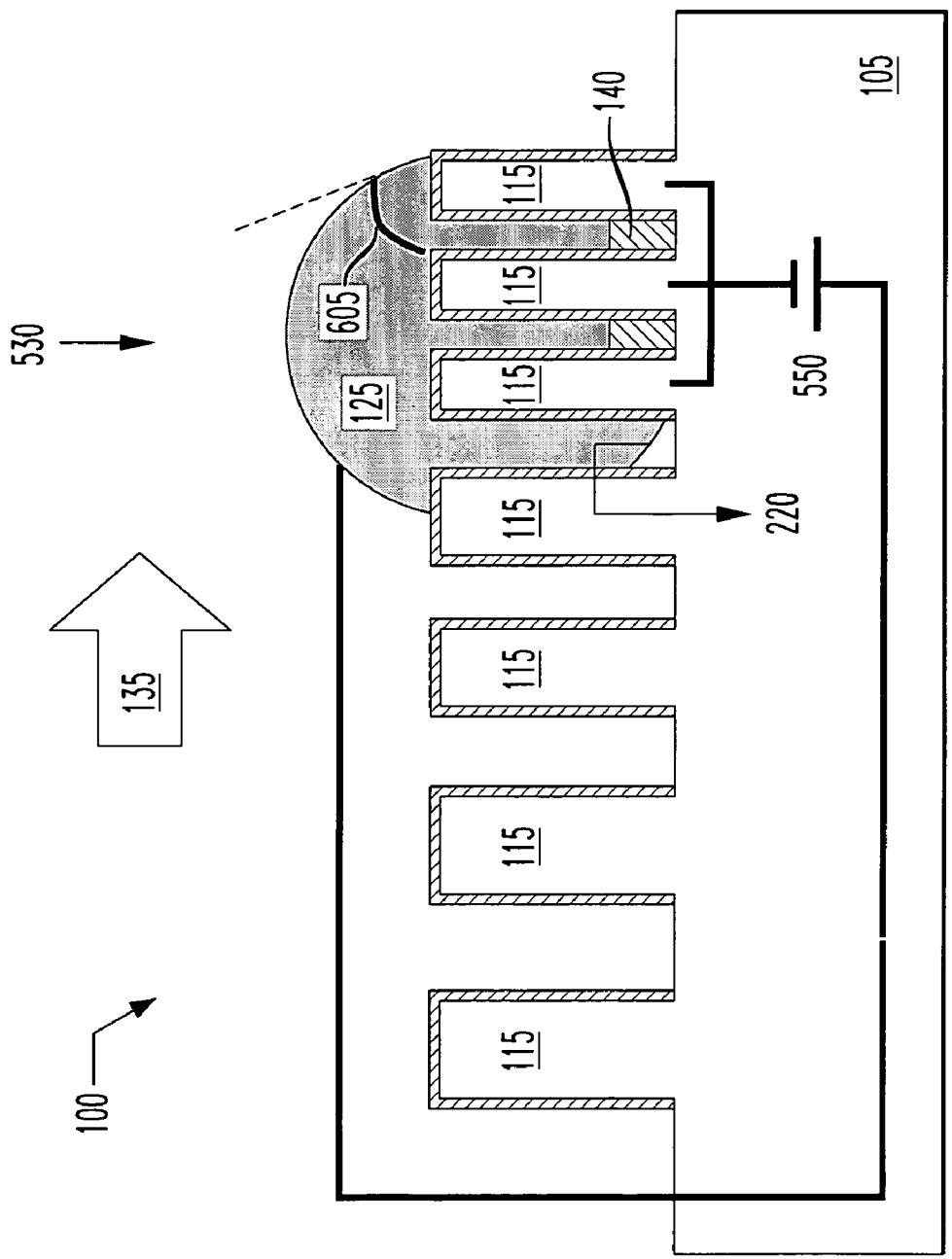

Turning now to FIG. 6, while maintaining reference to FIGS. 1-2 and 4-5, shown is the device 100 after electrowetting the sample 125 to thereby draw the sample 125 to the analytical depot 140. Electrowetting comprises applying a voltage 550 between the sample 125 and the sample-support-structures 115 in the vicinity of the analytical depot 140. If a high enough voltage 550 is applied, the sample 125 will penetrate the interior of the sample-support-structures 115 as shown in FIG. 6. In some cases, the applied voltage 550 is sufficient to lower the contact angle 605 of the sample to less than about 140 degrees and more preferably, to less than about 90 degrees. After the sample 125 contacts the analytical depot 140, various conventional processes can be performed to analyze the sample 125, to determine the sample's identity or some property of the sample.

Figure 7:
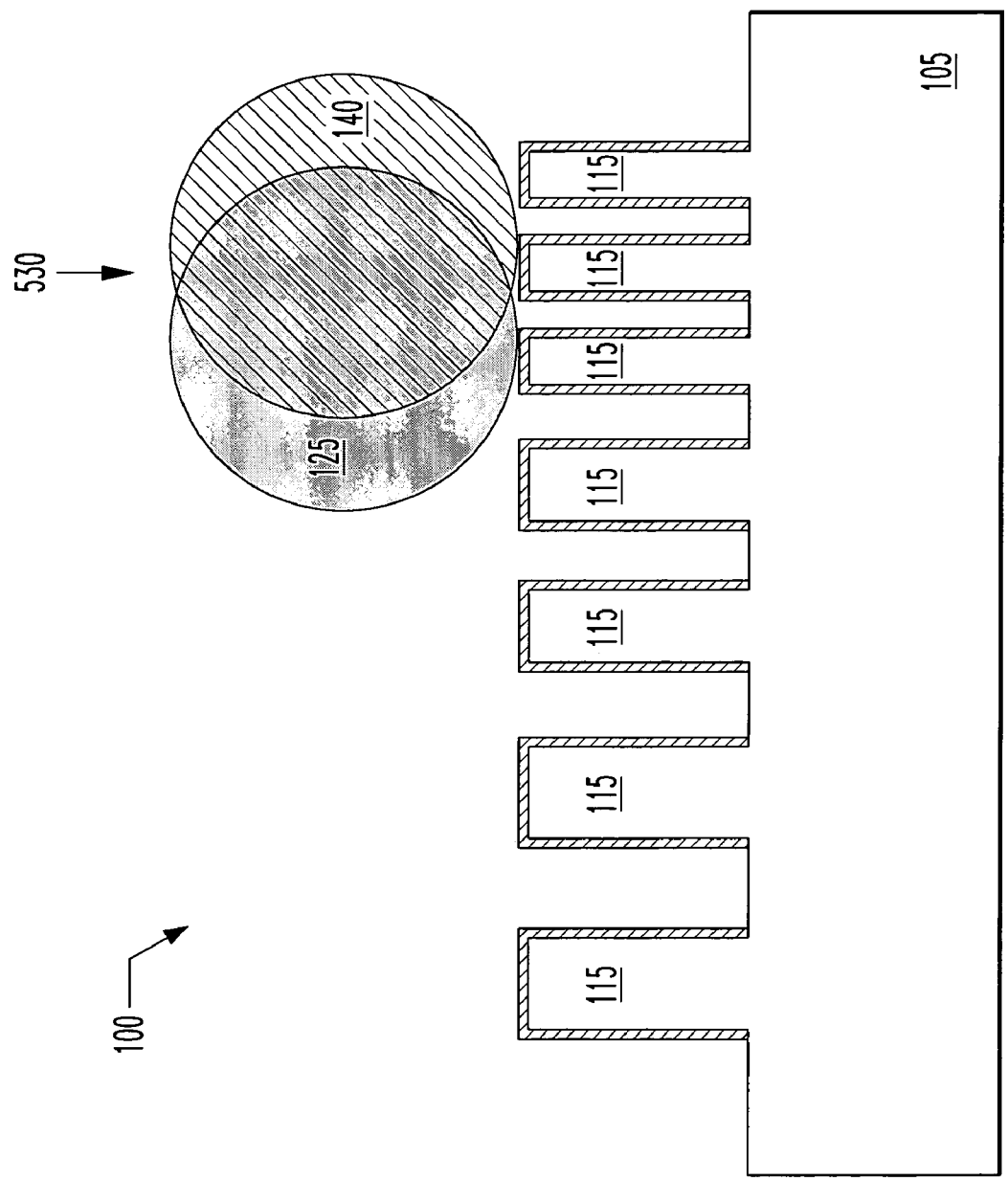

It should be understood that the analytical depot 140 does not have to be located at the floor 220 around certain sample-support-structures 115, and the sample does not have to be moved down to the analytical depot, such as depicted in FIG. 6. In alternative embodiments of the device 100, such as illustrated in FIG. 7, a fluid analytical depot 140 is located on the contact surfaces 130 of selected sample-support-structures 115 in the vicinity of the terminus 530. In some cases, the fluid 140 comprises compounds configured to react with the sample 125. By moving the sample 125 to the terminus 530, the sample 125 and fluid of the analytical depot 140 are mixed, thereby facilitating sample analysis. Of course, in still other embodiments of the device 100, a fluid analytical depot 140 can be moved to a stationary sample, or both the sample and analytical depot can moved to the terminus or other mixing point.

Figure 8:
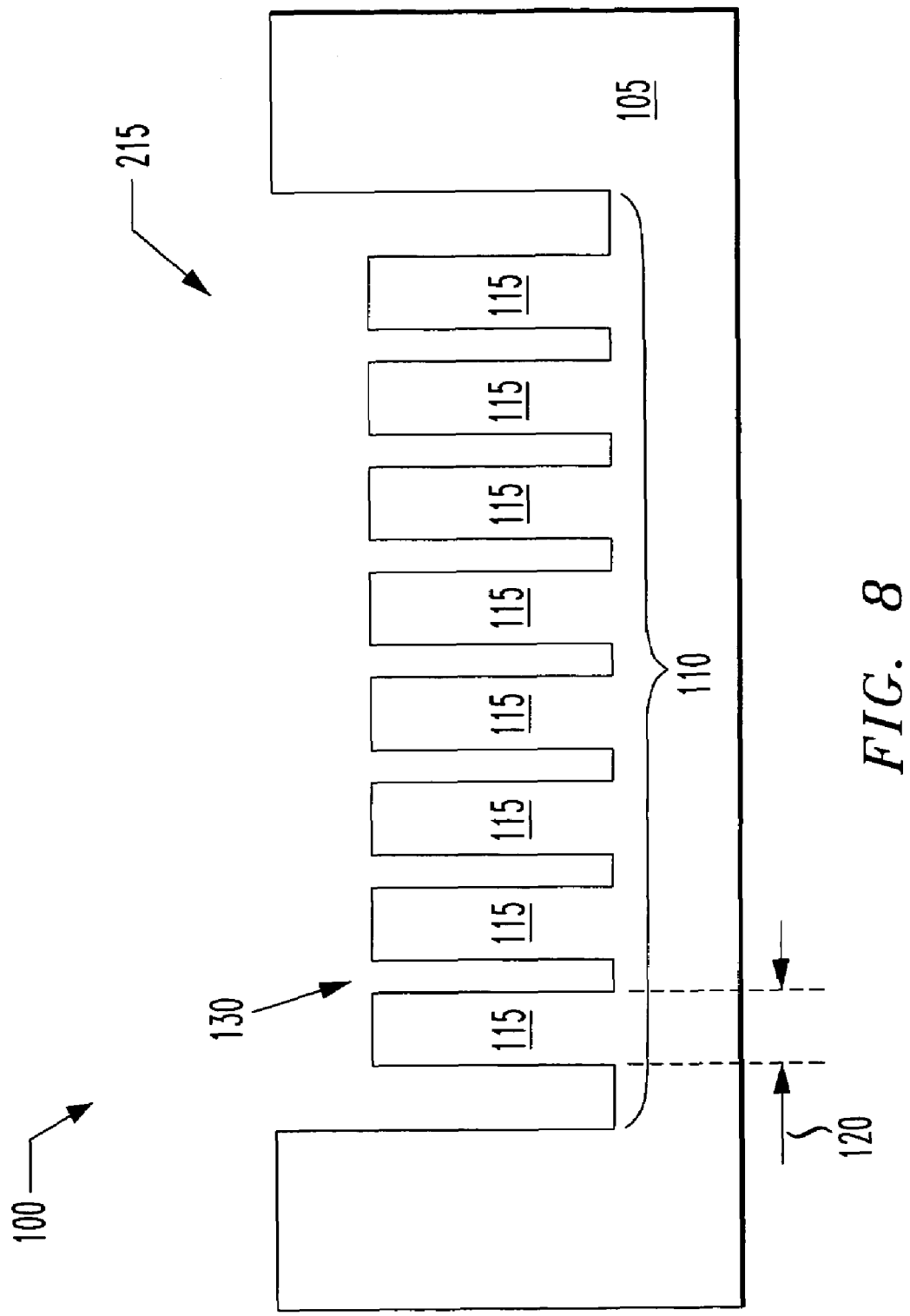
FIGS. 8-10 present cross-section views of an exemplary device shown in FIG. 1, at selected stages of manufacture.
Figure 9:
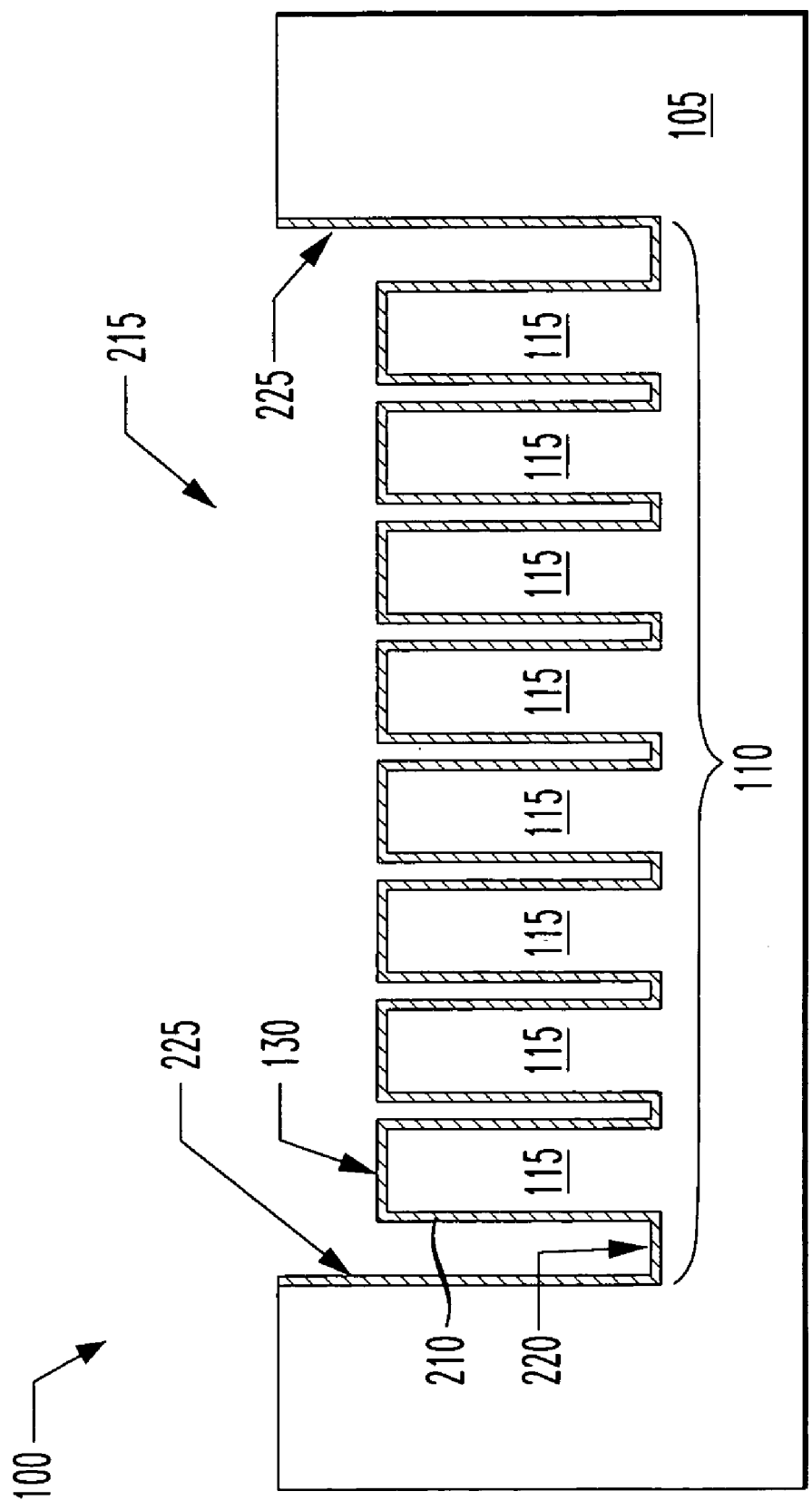
Figure 10:
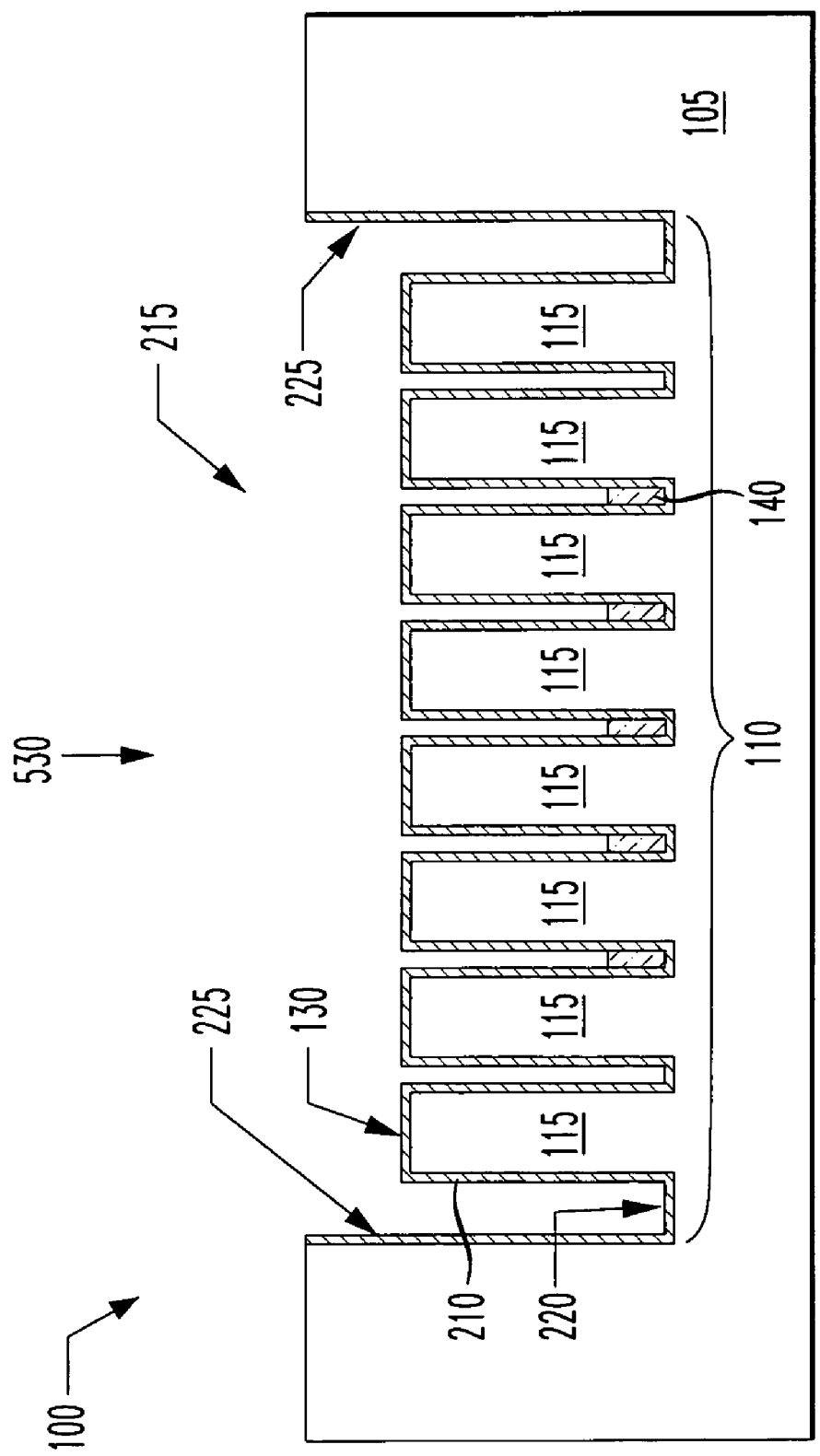

Still another aspect of the present invention is a method of manufacturing a device. FIGS. 8-10 present cross-section views of an exemplary device 100 at selected stages of manufacture. The cross-sectional view of the exemplary device 100 corresponds to view line 8-8 in FIG. 1. The same reference numbers are used to depict analogous structures shown in FIGS. 1-2 and 4-7. Any of the above-described embodiments of devices can be manufactured by the method.

Turning now to FIG. 8, shown is the partially-completed device 100 after forming a plurality of sample-support-structures 115 on a region 110 of an analytical substrate 105. Similar to the devices discussed in the context of FIGS. 1-7, each of the sample-support-structures 115 of the device 100 have at least one dimension 120 of about 1 millimeter or less. Additionally, a sum of areas of the contact surfaces 130 of the structures 115 is substantially less than a total area of the region 110, and the areas of the contact surfaces 130 define a prescribed sample path 135.

In some preferred embodiments the analytical substrate 105 is a planar semiconductor substrate, and more preferably, a silicon-on-insulator (SOI) wafer. Of course, in other embodiments, the substrate 105 can comprise a plurality of planar layers made of other types of conventional materials that are suitable for patterning and etching. The sample-support-structures 115 can be formed in the substrate 105 using any conventional semiconductor patterning and etching procedures well-known to those skilled in the art. Patterning and etching can comprise photolithographic and wet or dry etching procedures, such as deep reactive ion etching. In some embodiments, a channel 215 is formed in the substrate 105 using similar, and preferably the same, semiconductor patterning and etching procedures used to form the sample-support-structures 115.

Referring now to FIG. 9, while maintaining reference to FIG. 8, depicted is the partially-completed device 700 after coating each of the sample-support-structures 115 with an optional anti-adsorption layer 210. Preferably, the anti-adsorption layer 210 forms a conformal coating on the sample-support-structures 115. In some preferred embodiments, such as illustrated in FIG. 9, the anti-adsorption layer 210 coating also comprises conformally coating the floor 220 and walls 225 of the channel 215. In some embodiments, coating comprises spraying the sample-support-structures 115 with polyethylene glycol followed by curing to form the anti-adsorption layer 210. Of course other methods, well-known to those skilled in the art, can be used to form the anti-adsorption layer 210. For example, the anti-adsorption layer 210 can be covalently attached to the sample-support-structures 115 as a self-assembled monolayer by exposing the surface of the sample-support-structures 115 to a solution of PEG-functionalized thiol molecules, when the sample-support-structures 115 are composed of a metal or covered with a metallic layer. Alternatively, the anti-adsorption layer 210 can be covalently attached to the sample-support-structures 115 by exposing the surface of the sample-support-structures 115 to a solution of PEG-functionalized silane molecules, when the sample-support-structures 115 comprise silicon or silicon oxide.

Turning now to FIG. 10, while maintaining reference to FIGS. 8-9, illustrated is the device 100 after forming an analytical depot 140 located on the analytical sample substrate 105 and at a terminus 530 of the prescribed sample path 135. The analytical depot 140 can be formed by depositing a fluid reagent on sample-support-structures 115 in the vicinity of the terminus 530 and electro-wetting the fluid reagent to bring it to the floor 220 of the substrate 105. In other embodiments, the analytical depot 140 can be formed by constructing an organic field-effect transistor (OFET) at the terminus 530 in the substrate 105, using conventional procedures well known to those skilled in the art.

Although the present invention has been described in detail, those of ordinary skill in the art should understand that they could make various changes, substitutions and alterations herein without departing from the scope of the invention.

What is claimed is:

1. A device comprising:
a substrate having at least one region that comprises a plurality of structures for supporting a sample droplet on end contact surfaces thereof, each of said structures having at least one dimension of about 1 millimeter or less, wherein a sum of areas of said end contact surfaces of said structures is substantially less than a total area of said region and wherein said end contact surfaces define a prescribed lateral sample path for said sample droplet supported by said end contact surfaces, to an analytical depot located on said substrate, each one of said end contact surfaces being an end surface of one of said structures, and wherein a total area of said end contact surfaces per unit area of said region increases in a direction along said prescribed sample path towards said analytical depot.

2. The device of claim 1, wherein said sum of areas of said end contact surfaces is about 10 percent or less than said total area of said region.

3. The device of claim 1, wherein said sum of areas of said end contact surfaces is about 1 percent or less than said total area of said region.

4. The device of claim 1, wherein at least about 90 percent of solid surfaces that said sample droplet contacts corresponds to said end contact surfaces.

5. The device of claim 1, wherein each of said structures is coated with an anti-adsorbing layer.

6. The device of claim 1, wherein each of said structures comprises a post and said one dimension is a lateral thickness of said post.

7. The device of claim 1, wherein each of said structures comprises a cell and said at least one dimension is a lateral thickness of a wall of said cell.

8. The device of claim 1, wherein said prescribed sample path is in a channel and said region comprises an interior surface of said channel.

9. The device of claim 8, wherein said channel has a width ranging from about 100 to about 10 microns.

10. The device of claim 8, wherein said channel has a slip length that is at least about 10 percent of a width of said channel.

11. The device of claim 1, wherein each of said end surfaces correspond to an uppermost 1 to 10 percent of said structures.

12. The device of claim 1, wherein said analytical depot is located on a different surface of said substrate than said end contact surfaces.

13. The device of claim 1, wherein said analytical depot includes a reagent-containing fluid droplet supported by selected ones of said end contact surfaces located at a terminus of said prescribed sample path.

14. The device of claim 1, wherein a density of said structures increases in a direction along said prescribed sample path towards said analytical depot.

15. The device of claim 1, wherein a diameter of said structures increases in a direction along said prescribed sample path towards said analytical depot.

16. The device of claim 1, wherein a spacing between said structures decreases in a direction along said prescribed sample path towards said analytical depot, and, a diameter of individual ones of said structures remains constant in said direction.

17. The device of claim 1, wherein said sample droplet forms a contact angle with said end contact surfaces of about 140 degrees or higher.

* * * * *